(12) United States Patent
Williams et al.

(10) Patent No.: US 10,139,321 B2
(45) Date of Patent: Nov. 27, 2018

(54) MUCOLYTIC TABLET FOR A SAMPLE COLLECTION DEVICE

(71) Applicant: ALPHA-TEC SYSTEMS, INC., Vancouver, WA (US)

(72) Inventors: Richard Williams, Vancouver, WA (US); Anne Frontella, West Linn, OR (US); Mark Williams, Vancouver, WA (US)

(73) Assignee: Alpha-Tec Systems, Inc., Vancouver, WA (US)

( * ) Notice: Subject to any disclaimer, the term of this patent is extended or adjusted under 35 U.S.C. 154(b) by 96 days.

(21) Appl. No.: 15/224,160

(22) Filed: Jul. 29, 2016

(65) Prior Publication Data

US 2018/0031455 A1 Feb. 1, 2018

(51) Int. Cl.
*G01N 33/15* (2006.01)
*G01N 1/38* (2006.01)
*B01L 3/00* (2006.01)

(52) U.S. Cl.
CPC .............. *G01N 1/38* (2013.01); *B01L 3/52* (2013.01); *G01N 33/15* (2013.01)

(58) Field of Classification Search
CPC .................................................. G01N 33/15
See application file for complete search history.

(56) References Cited

U.S. PATENT DOCUMENTS

| | | | |
|---|---|---|---|
| 4,425,438 A | 1/1984 | Bauman et al. | |
| 4,652,520 A | 3/1987 | Bauman | |
| 5,807,756 A | 9/1998 | Bauman et al. | |
| 5,830,767 A | 11/1998 | Bauman et al. | |
| 6,475,523 B1* | 11/2002 | Staniforth | A61K 9/0075 424/45 |
| 6,623,754 B2 | 9/2003 | Guo et al. | |
| 9,138,747 B2 | 9/2015 | Williams et al. | |
| 2003/0083286 A1* | 5/2003 | Teng | A61K 9/2077 514/44 A |
| 2003/0129679 A1 | 7/2003 | Siddiqi | |
| 2006/0030550 A1* | 2/2006 | Lithgow | A61K 31/4245 514/171 |
| 2013/0248045 A1* | 9/2013 | Williams | A61B 10/0045 141/1 |

FOREIGN PATENT DOCUMENTS

| | | | | |
|---|---|---|---|---|
| CA | 1184114 A | 3/1985 | | |
| DE | 3627501 A1 | 2/1988 | | |
| EP | 0060700 A1 | 9/1982 | | |
| EP | 0339508 A1 * | 11/1989 | ........... A61K 9/0056 | |
| EP | 1329718 A1 | 3/2007 | | |
| WO | 9621508 A1 | 7/1996 | | |

* cited by examiner

*Primary Examiner* — Paul S Hyun
(74) *Attorney, Agent, or Firm* — McCoy Russell LLP

(57) ABSTRACT

The present disclosure relates to a mucolytic tablet for a sample collection device that causes mucolysis of biological samples collected in the sample collection device. The mucolytic tablet includes N-acetyl L-cysteine (NALC), a pharmaceutically active mucolytic agent that reduces the viscosity of mucus containing biological samples. The mucolytic tablet also includes one or more chelating agents, water-soluble anti-adherent/s, and at least one buffering agent.

21 Claims, 4 Drawing Sheets

MUCOLYTIC TABLET FOR A SAMPLE COLLECTION DEVICE

FIELD OF INVENTION

The present description relates to composition of a tablet for homogenizing a biological sample collected in a sample collection device.

BACKGROUND

Biological samples, such as body fluids, are often collected for testing and/or analysis. Testing and/or analysis of the biological samples may assist in diagnosis of many ailments. Often, the biological sample may be collected in a sample collection device, stored, and transported in the sample collection device for further analysis. The sample collection device may include certain chemical reagent/s to stabilize, pre-process, and/or to process the collected biological sample during storage in the sample collection device. The chemical agents may be present in form of granules, capsules, loose powder, liquid, or tablets inside the sample collection device.

In one example, a mucolytic agent, such as N-acetyl-L-cysteine (NALC) in a tablet form may be present inside a sample collection device. When a biological sample, such as sputum, may come in contact with NALC inside the sample collection device, NALC may reduce viscosity of the biological sample, making the biological sample suitable for further analysis.

However, the inventors herein have recognized problems with the above-mentioned approach, including constituents of the NALC tablet not solubilizing completely, and certain constituents in the NALC tablet interfering with molecular reactions such as antibody-based analysis of the biological sample, and/or DNA detection in the biological sample by polymerase chain reaction (PCR). Additionally, the tablet may include constituents, which may alter microbial survivability either by being a food source or by being toxic to certain types of microbes present in the biological sample, thereby interfering with accurate analysis of the biological sample.

The inventors herein propose a composition for a mucolytic tablet for a sample collection device, including 15% to 65% by weight of N-acetyl L-cysteine (NALC), 6% to 30% by weight of a buffering agent, 10% to 14% by weight of a water soluble anti-adherent, and 2% to 10% by weight of at least one chelating and lubricant agent, wherein the mucolytic tablet solubilizes in a resuspension buffer. The resuspension buffer may include between 60 mM to 67 mM phosphates, and 56-60 mM sodium citrate. In one example, the phosphates of the resuspension buffer may be from 30-36 mM disodium hydrogen phosphate and 30-36 mM dipotassium hydrogen phosphate. A weight of the mucolytic tablet may range between 0.045-0.055 grams and a time for dissolving the mucolytic tablet in 3-6 ml of the resuspension buffer may be between 1.00-1.3 minutes. NALC in 3-6 ml of resuspension buffer with the dissolved mucolytic tablet may be between 4-6 mg/ml and a pH of the resuspension buffer with the dissolved mucolytic tablet may be between 6.2-6.5.

An example method for preparing a mucolytic tablet may include premixing constituents of a mucolytic tablet, followed by desiccating the premixed constituents, the premixed constituents including 15% to 65% by weight of N-acetyl L-cysteine (NALC), 6% to 30% by weight of a buffering agent, 10% to 14% by weight of a water-soluble anti-adherent, 2% to 10% by weight of at least one chelating and lubricating agent, and preparing the mucolytic tablets from the desiccated premixed constituents. Desiccating the premixed constituents may include desiccating under vacuum between 26° C. to 28° C. for 20 hours-2 weeks. Preparing the mucolytic tablet may include use of a tablet-punching machine at a speed between 25.5-40.5 g/second with a compression force between 3.5-4.5 pascal.

In one example, a sample collection device may include a container with a closure assembly, a reagent chamber inside the container, the reagent chamber fluidically connected to an inner volume of the container, and a mucolytic tablet in the reagent chamber, wherein a composition of the mucolytic tablet may include 15% to 65% by weight of N-acetyl L-cysteine (NALC), 6% to 30% by weight of $K_2HPO_4$, 10% to 14% by weight of L-Leucine, 2% to 10% by weight of polyethylene glycol, and 0% to 60% by weight of trisodium citrate.

In this way, a mucolytic tablet, including a mucolytic agent NALC, may be dissolved in a resuspension buffer. Upon mixing of the resuspension buffer with a sample collected in a sample collection device, the NALC of the mucolytic tablet may act to reduce the viscosity of the sample. Reduction in viscosity of the sample may make the sample conducive for mixing with additional reagents for forming a homogeneous solution during subsequent analysis for accurate diagnosis of various disease conditions. The formulation of the mucolytic tablet and the composition of the resuspension buffer are configured such that there is no interference with molecular assays and microbial survivability.

DETAILED DESCRIPTION

N-acetyl L-cysteine (NALC) is a pharmaceutically active mucolytic agent, which reduces the viscosity of biological samples containing mucus. Mucus is produced from various mucous membranes inside the body, for example, by mucous membranes in the respiratory system of the body, in the digestive system of the body, etc., both during normal health as well as during certain disease conditions. Diagnostic testing of the biological sample containing mucus may be done for identifying disease conditions including but not limited to, bronchitis, sinusitis, rhinitis, pneumonia, tuberculosis, etc. In one example, the disease condition may be caused by a bacterial infection of the respiratory tract (for example, *Mycobacterium tuberculosis* infection), or viral infection of the respiratory system (for example, Rhinovirus induced viral rhinitis). In other examples, other microorganisms, including fungi and parasites, may cause the disease condition.

The biological sample may be collected in a sample collection device. The biological sample may be of human origin or may be of animal origin. The biological sample collected may be viscous due to presence of mucus in the sample. To enable the use of the biological sample for diagnostic tests, viscosity of the biological sample may be reduced for homogenous mixing with reagents of the diagnostic test. To reduce viscosity of the biological sample a reagent may be placed inside the sample collection device, the reagent including a mucolytic compound. In one example, the reagent in the sample collection device may be in granular form, liquid form, powder form, tablet form etc. and may act on the collected biological sample to reduce viscosity of the biological sample and increase homogenization.

In one example, the reagent inside the sample collection device may be a tablet containing a mucolytic compound. In one example, the mucolytic compound in the tablet may be from at least one member selected from the group consisting of guiafenesin. N-acetyl-L-cysteine (NALC), and dithiothreitol. In an example, the mucolytic compound in the tablet may be NALC.

Additionally, the tablet may include a chelating agent, wherein the chelating and lubricating component may be at least one member selected from the group consisting of ethylene diamine tetraacetic acid, ethylene glycol tetraacetic acid, trisodium citrate, and nitrilotriacetic acid. In one specific example, the chelating agent in the tablet may be polyethylene glycol. In another example, the chelating agent may be trisodium citrate. In a further example, both trisodium citrate and polyethylene glycol may be present in the tablet.

The tablet may also include a buffering agent to maintain a pH when the tablet is in solution, as the pH is conducive for the biological sample and constituents of the tablet to remain active. The pH may be maintained close to the neutral pH 7, for example, pH between 6.5-7.2, such that the biological sample is not exposed to very high and/or very low pH, which may compromise the integrity of biologically active components of the biological sample. The buffering agent may be at least one from the specified group of buffering agents, including hydrochloric acid, sodium hydroxide, potassium hydroxide, dipotassium phosphate, monopotassium phosphate, and sodium carbonate. In one specific example, the buffering agent in the tablet may be dipotassium phosphate.

A water-soluble anti-adherent agent may be present in the tablet to ease the formation of the tablet during manufacturing. Anti-adherents present in the tablet may prevent the tablet form sticking, for example, to a tablet-making machine while preparing the tablet. Example of anti-adherent water-soluble agents include L-Leucine, cornstarch etc. The composition of the tablet will be discussed further with reference to Table 1.

Solubilization of the tablet in a resuspension buffer may release all the constituents of the tablet, including NALC into the resuspension buffer. NALC released from the tablet may act on the biological sample, reducing the viscosity of the mucus in the biological sample. Solubility of the tablet in the resuspension buffer and a concentration and activity of each of the constituents of the tablet upon solubilization may be important for optimal action on the biological sample collected in the sample collection device. The constituents of the resuspension buffer will be discussed below with reference to Table. 2.

Figure 1:
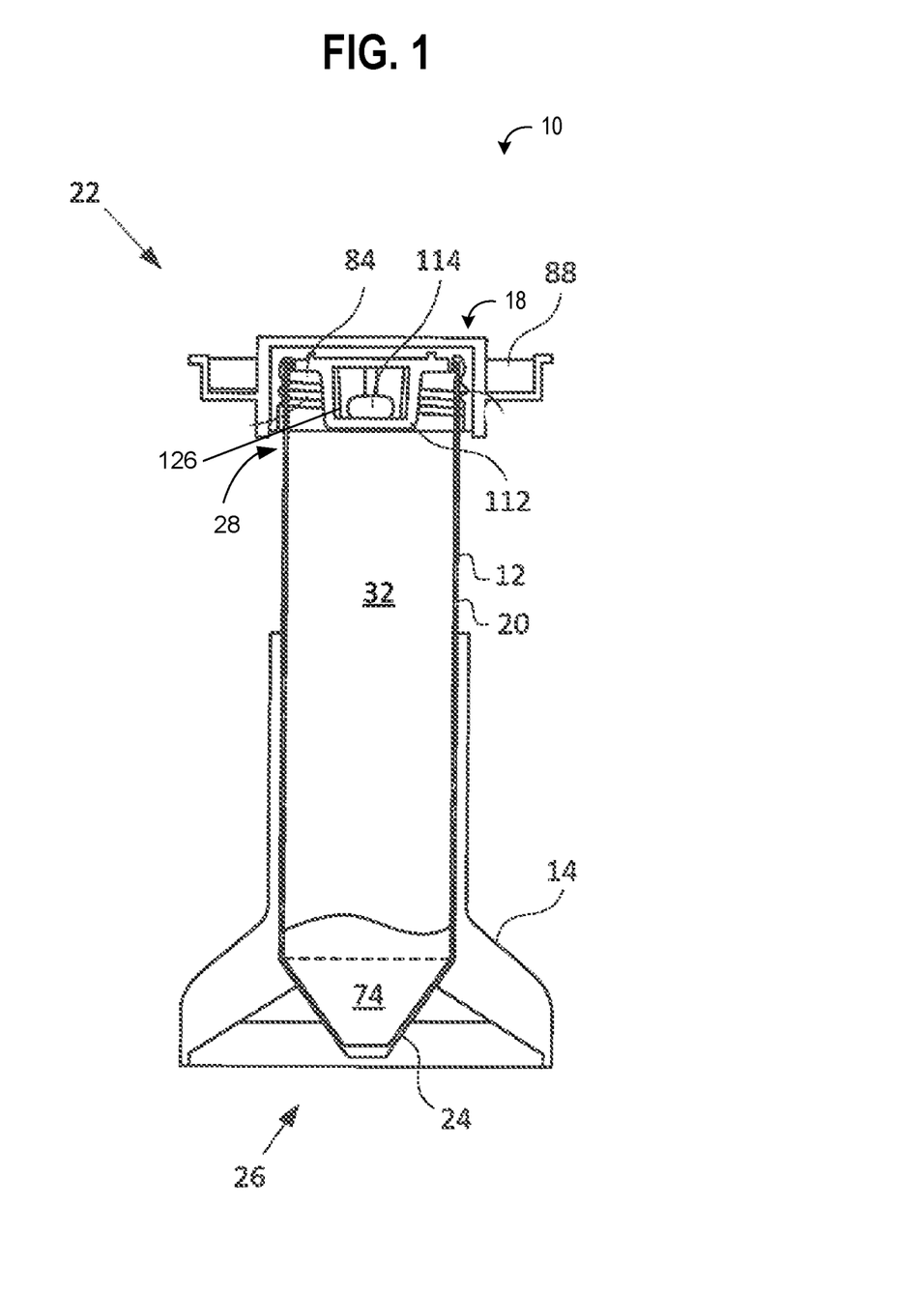
FIG. 1 illustrates a mucolytic tablet inside a reagent housing of a sample collection device.

FIG. 1 illustrates a non-limiting example of a sample collection device 10 in a cross-sectional view. The sample collection device 10 may include a container 12, a base 14, a reagent housing 112, and a closure assembly 18. In one example, various components of the sample collection device 10 may be constructed of clear or colored injection molded polymers.

The container 12 may be any suitable container for receiving and retaining a biological sample, such as a bodily fluid containing mucus. The container 12 may include an upper portion 20 at a first or upper end 22 and a lower portion 24 at a second or lower end 26. In one example, the upper portion 20 may be generally cylindrical with a substantially circular cross-section, and may include an opening 28. The lower portion 24 may depend from upper portion 20, may be generally conical, and/or may include a closed lower end 26. In some embodiments, the upper portion 20 may have a generally rectangular cross-section, or any other suitable shape. In some embodiments, the lower portion 22 may be truncated, flat, rounded, or any other suitable shape forming a lower closed end of the container 12. The lower end 26 of container 12 may be supported by the base 14. The base 14 may include any suitable structure configured to receive and support the container 12 and to generally bias the container against tipping.

The container 12 may be a graduated test tube or a vial. The container 12 may be translucent and may be of any suitable size. For example, the container 12 may be one or more standard sizes used in laboratory analyses (e.g., 50 ml). The container 12 may include the closure assembly 18, disposed proximate to an opening 28 of the container 12.

The opening 28 of the container 12 may be configured to couple to the closure assembly 18. In one example, the closure assembly 18 may be coupled to the opening 28 by threading a cap 84 onto an upper end 22 of the sample collection device 10. As illustrated in FIG. 1, a lid 88 may remain attached to the cap 84. The lid 88 may be manually rotated to thread the cap 84 onto the container 12 because of textured surfaces (not shown) interacting to substantially prevent the lid and the cap from rotating relative to each other, while still allowing manual removal of the lid 88 from cap 84 using axial and/or oblique force.

A reagent housing 112 may be any suitable structure operatively attached to and disposed within the closure assembly 18, and configured to releasably contain or retain a reagent 114. Specifically, the reagent housing 112 may include a chamber configured to be in fluid communication with an interior portion 32 of container 12 when opening 28 is sealed by the closure assembly 18. The reagent housing 112 may include a structure herein referred to as a cage 126. The reagent housing 112 may be disposed, attached, and/or hermetically sealed adjacent an inside surface of the cap 84 for releasably retaining the reagent 114, such as a dissolvable tablet. Although the following description refers to a reagent housing for retaining a reagent including a dissolvable tablet or tablets, the reagent 114 may include one or more of granule(s), liquid(s), tablet(s), capsule(s), chemical reagent coating(s), etc. The reagent may be dissolvable or non-dissolvable. In one example, the reagent 114 may be soluble in a resuspension buffer. Additionally, the reagent may be any suitable size(s) and/or amount(s). Moreover, the reagent may contain from one chemical to several chemicals to complete any required reaction(s).

The reagent housing 112 may extend from an inside surface of the cap 84. The reagent housing 112 may be rigid or semi-rigid, and may be held to the cap using glue or other joining method, such as ultrasonic welding. Any suitable joining method capable of withstanding forces experienced during, for example, sample centrifugation may be used. The reagent housing may include the cage 126 including one or more apertures radially extending along the lateral periphery and/or one or more apertures disposed at the bottom surface of the reagent housing. The apertures may be smaller than reagent 114, such that when the reagent is a dissolvable tablet, the dissolved tablet may flow through the apertures to the interior of the container 12 and/or the apertures may be sized to allow an influx and out flux of adjacent specimen 74 inside the container 12. During use, some or all of the specimen 74 may pass in and out of reagent housing 112 to dissolve the reagent 114. In other examples, reagent 114 may be described as passing through the apertures to communicate or mix with the specimen 74.

In other embodiments, a removable seal (not shown) may be attached to the closure assembly 18 to prevent accidental reagent leakage and/or contamination or other adverse effects on the reagent. For example, a removable seal (not shown) may be attached directly to a lower periphery of the cap 84 such that the reagent housing, reagent specific atmosphere, and/or reagent are sealed within the cap 84.

In one example, the sample collection device 10 may include a funnel (not shown), which may be removably attachable or mountable to the container 12. The funnel may be configured to be secured to the opening 28 of the container 12. The funnel may be any suitable structure configured to facilitate and direct placement of a sample into the container 12 through the opening 28.

The reagent 114 may include multiple reagents or chemicals in compressed tablet form (or chemical reagent coating(s), granule(s), capsule(s), etc.) and/or may include one or more of the following components: a mucolytic agent used to disrupt disulfide bonds, a chelating component used to sequester inhibitory ions, a pH altering reagent(s) to achieve and maintain neutrality of the specimen during transport to the laboratory, and/or necessary excipients for tablet formulation and stability. The excipients may include one or more water-soluble anti-adherent agents. The homogenization agent, for example, may be used as a pretreatment for sputum in a method of detecting a microbe (or microbes).

The mucolytic compound may include guiafenesin. N-acetyl-L-cysteine, dithiothreitol, and/or other suitable mucolytic compound(s). The chelating and lubricating component may include ethylenediaminetetraacetic acid, polyethylene glycol, trisodium citrate, nitrilotriacetic acid, and/or other suitable chelating and lubricating component(s). The pH altering reagents may include hydrochloric acid, sodium hydroxide, potassium hydroxide, dipotassium phosphate, monopotassium phosphate, sodium carbonate, and/or other suitable pH altering reagent(s). Additionally and/or alternatively, the pH-altering reagent may render a final pH of a biological sample to be neutral and/or between a pH of about 6.5 to a pH of about 8.1. The water-soluble anti-adherent agent may include L-Leucine, cornstarch and/or any other suitable excipient(s).

The reagent from the reagent housing may be introduced into the container 12 to be in contact with the specimen 74. In one example, the closure assembly 18 may be coupled to the opening 28 without dispensing the reagent 114 from the reagent housing into the container 12 with the specimen 74. The reagent 114 may be disposed into the container 12 at a later point of time. In other example, the reagent 114 may be present inside the container 12 before the introduction of the specimen 74 into the container 12. In another example, buffers, and solutions, for example, a resuspension buffer may be introduced to the container 12 before or after sample collection to work in combination with the reagent 114. The buffers and or the biological sample may be mixed by inverting and/or shaking the sample collection device.

The reagent 114 may be a tablet, the tablet including a mucolytic agent, a buffering agent, an anti-adherent agent, and one or more chelating and lubricating agents. A composition of the tablet is provided in Table 1 below.

TABLE 1

Composition of the tablet

| Constituent | Percentage (by weight) |
|---|---|
| N-acetyl L-cysteine | 15%-65% |
| $K_2HPO_4$ | 6%-30% |
| L-Leucine | 4%-15% |
| Polyethylene glycol | 2%-10% |
| Trisodium citrate ((TSC) | 0%-60% |

The mucolytic agent in the tablet may be NALC. Typically, the tablet may contain NALC in the range of 15%-65% by weight. More typically, the tablet may include NALC between ranges of 55%-65% by weight. The amount of NALC in the tablet may be further varied with in the specified ranges. NALC used for the tablet maybe a medium grade NALC (90% of NALC particles between 100-500 micron size). In other examples, the NALC may be fine grade (50% of NALC particles less than 100 micron).

A buffering agent present in the tablet may maintain a pH of a solution when the tablet is dissolved in the solution. The buffering agent may be a source of phosphate, for example, K2HPO4. The buffering agent $K_2HPO_4$ may be present in an amount in the range of 6%-30% by weight of the tablet. In another example, $K_2HPO_4$ may be in the range of 20%-30% by weight of the tablet. In a further example, $K_2HPO_4$ may be between 21%-25% by weight of the tablet.

$K_2HPO_4$ maintains the pH of the biological sample in the sample collection tube at close to a physiological pH, for example, within the pH range of 6.2-7.5. In an example, the pH may be in the range of 6.3-7. In yet another example, the pH may be 6.4-7.

The tablet may include one or more water-soluble anti-adherent agent. One example of an adherent agent is L-Leucine (AMRESCO). L-Leucine is a water-soluble lubricant with anti-adherent properties. L-Leucine may prevent the tablets from sticking during preparing process and during storage of the tablet. L-Leucine may be present in the broader range of 4%-15% by weight in the tablet. In one example, L-Leucine may be present between the range of 11%-13%, and more specifically may be present 11.5%-12.5% by weight in the tablet.

In addition, the tablet may include one or more chelating and lubricating agent which may be selected from but are not limited to those conventionally known in the art such as polyethylene glycol, glycerol monostearate, glyceryl monosterate, glyceryl behenate, mineral oil, sodium stearyl fumarate, stearic acid, hydrogenated vegetable oils, sodium citrate. In one example, the tablet may contain polyethylene glycol (PEG 4600 from DOW chemicals). The polyethylene glycol may constitute 2%-10% by weight of the tablet. In another example, a range of polyethylene glycol by weight in the tablet may be 4%-6%. In yet another example, 4.5%-5.5% of the tablet by weight may be polyethylene glycol.

The tablet may also include another chelating agent, for example, trisodium citrate (TSC). In an example, the tablet may contain 0%-60% by weight of TSC. In one example, the\range of TSC by weight in the tablet may be 0%-10%. In another example, 0.5%-2% of the tablet by weight may be TSC.

The above-described constituents of the tablet may be weighed and premixed before being formed into the tablets. The premixed constituents of the tablet may be desiccated before being formed into tablets.

It is understood that the sample collection device including the tablet in the reagent housing described and illustrated herein represents only an example embodiment. It is appreciated by those skilled in the art that various changes and additions may be made to such a sample collection device without departing from the spirit and scope of this invention.

Figure 2:
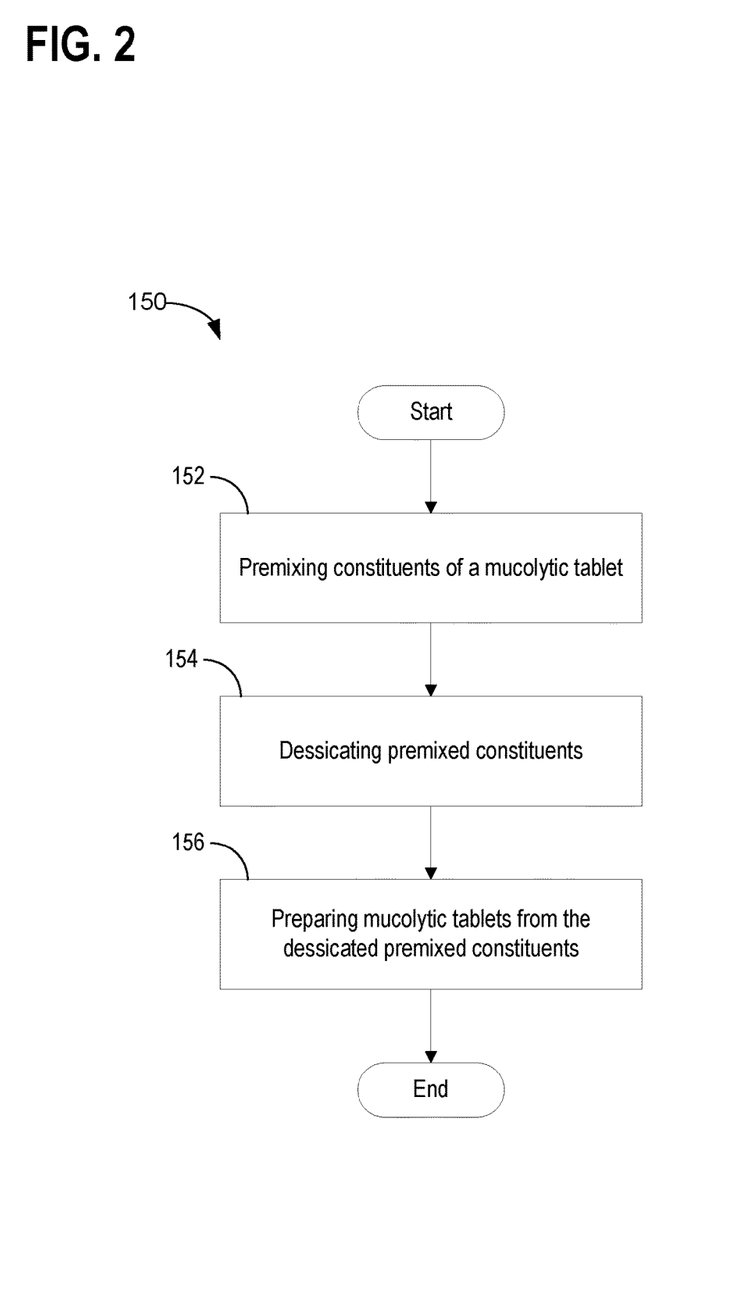
FIG. 2 shows a flow chart of a method for preparing the mucolytic tablet of FIG. 1.

FIG. 2 illustrates a flowchart of a method 150 for preparing a mucolytic tablet. The mucolytic tablet may be of the composition listed above in Table 1. In one example the mucolytic tablet once formed may be placed inside the reagent housing 112 of the sample collection device 10 illustrated in FIG. 1. In other examples, the mucolytic tablet may be placed in alternative embodiments of a sample collection device, which may or may not include a reagent housing. In a further example, the mucolytic tablet may be packaged in a kit intended for use in mucolysis of biological samples.

The method begins at 152 by premixing constituents for forming the mucolytic tablet. The mucolytic tablet constituents may be the constituents listed in Table 1. The proportion of NALC, the buffering agent, the water-soluble anti-adherent, and one or more of the chelating and lubricating agents may be within the ranges described above. In one example, the constituents of the mucolytic tablet may include 15-65% by weight of NALC, 6-30% by weight of $K_2HPO_4$, 4-15% by weight L-Leucine, 2-10% by weight of polyethylene glycol, and 0-60% by weight of TSC. Each of the constituents of the mucolytic tablet may be weighed and then all of the constituents may be mixed together, for example, by using a mixing device or manually.

After premixing the constituents of the mucolytic tablet, the method 150 proceeds to 154, where the premixed constituents are kept for desiccating to remove excess moisture from the premixed constituents. The desiccation time may range from 2 hours to 2 weeks. In one example, desiccation for 20 to 30 hours at ambient temperature (26° C. to 28° C.) under vacuum may be performed before preparing the tablets. Desiccating the premixed constituents reduces moisture content of the premixed constituents and may thereby enhance the integrity of the tablets (less sticky tablets, better binding of the tablets).

At 156, preparing of the mucolytic tablets from the desiccated premixed constituents of the mucolytic tablet is carried out. The tablets may be prepared by a manual press or by using a tablet press/machine, which may be automated. The tablet machine may punch tablet of desired diameter, such as 5 mm tablets. The tablets may be prepared by the tablet machine at a speed of 25.5-40.5 g/sec, and more specifically in the speed between 30.5-42.5 g/sec. A compression force applied by the tablet machine during the punching of the tablets may be in the range of 3.5-4.5 pascal. In one example, the tablet machine may prepare 5 mm tablets at the speed of 35-36 g/sec, preparing 24-26 tablets/minute. Each tablet may weigh between 0.045 to 0.055 g. In another example, the tablet may weigh between 0.46 g to 0.5 g. The method 150 then ends.

In one example, the punched mucolytic tablet may be placed inside a sample collection device, for example, in the reagent housing 112 of the sample collection device 10 illustrated in FIG. 1 and the closure assembly 18 may be coupled to the opening 28. During collection of the biological sample in the sample collection device, a resuspension buffer may be introduced into the sample-containing device to dissolve the mucolytic tablet. An example method describing collecting and homogenizing a biological sample in a sample collection device will be described below with reference to FIG. 4.

The mucolytic tablet may solubilize completely in the resuspension buffer to release all the constituents of the tablet into a solution. A formulation of the resuspension buffer, which may be ideal for dissolving the tablet, is shown below in Table 2.

TABLE 2

| Formulation of the resuspension buffer | |
|---|---|
| Constituent | Concentration (mM) |
| $Na_2HPO_4$ | 2-36 mM |
| $KH_2PO_4$ | 2-36 mM |
| TSC | 0-60 mM |

The resuspension buffer includes source of phosphates, for example, $KH_2PO_4$ and $Na_2HPO_4$ and one or more chelating agents. In an example, the chelating agent may be TSC. An example formulation of the suspension buffer may include 30-36 mM $Na_2HPO_4$, 30-36 mM $KH_2PO_4$, and 30-50 mM TSC. In another example, no TSC may be present in the resuspension buffer.

Figure 3:
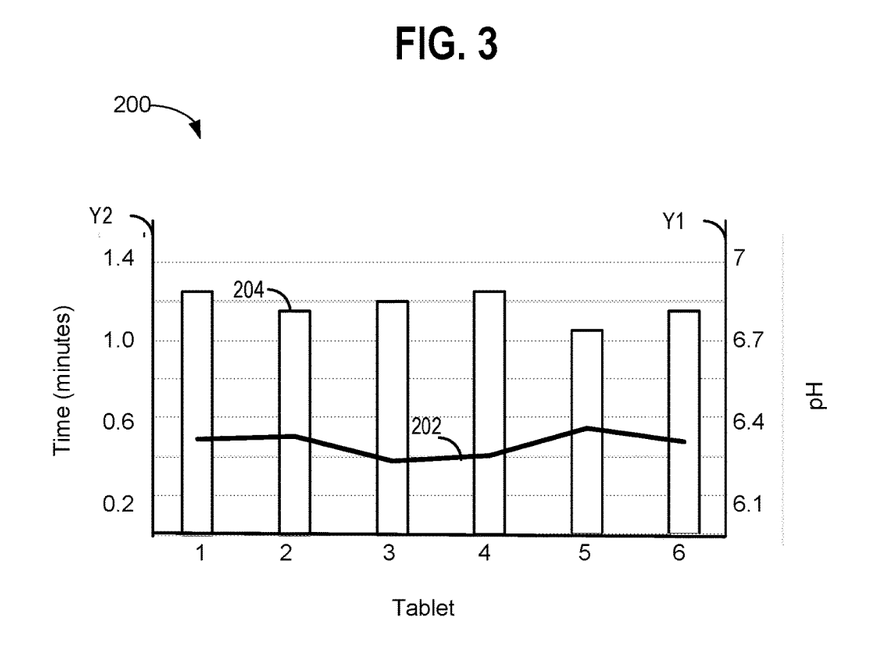
FIG. 3 shows a graph depicting a dissolution time and pH when the mucolytic tablet of FIG. 2 is dissolved in a resuspension buffer.

FIG. 3 illustrates a graph 200 showing a dissolution time in minutes (columns 204 along a first Y-axis Y1) of six tablets (tablets 1-6). Each tablet of the six tablets is dissolved in 6 ml of a resuspension buffer. After the dissolving of each tablet in the resuspension buffer, pH is illustrated along a second Y-axis Y2, and is indicated by a line 202. Each tablet is of the composition listed in Table 1, with a weight of the tablets ranging between 0.046-0.048 g. FIG. 3 will be further described below with reference to Example 1.

The formulation of the mucolytic tablet listed in Table 1 may be an effective mucolytic reagent for mucous containing samples of human or animal origin. The mucolytic tablet when added to a sample, for example, sample from the respiratory system (nasal discharge etc.), sample from the digestive system (fecal sample, vomit etc.), and/or sample from the reproductive system (semen, vaginal discharge etc.), the constituents of the mucolytic tablet may reduce the viscosity of the samples, making them more homogeneous. In lab studies conducted, the constituents of the mucolytic tablet showed none to minimal effect on growth and survivability of microbes, such as, *Escherichia coli, Pseudomonas aeruginosa, Klebsiella pneumoniae* etc., which may be present in the mucus containing samples.

The mucolytic tablet when stored at room temperature showed a surprisingly long and stable shelf life (of at least 30 months), as will be discussed below with reference to Example 2. Additionally, the mucolytic tablet dissolved in the resuspension buffer rapidly and completely at room temperature, enabling quick and easy mixing of the constituents of the mucolytic tablet with a collected biological sample in the sample collection device. The presence of constituents of the mucolytic tablet did not alter the sensitivity of molecular reactions, for example, PCR, as will be described below in Example 3.

Figure 4:
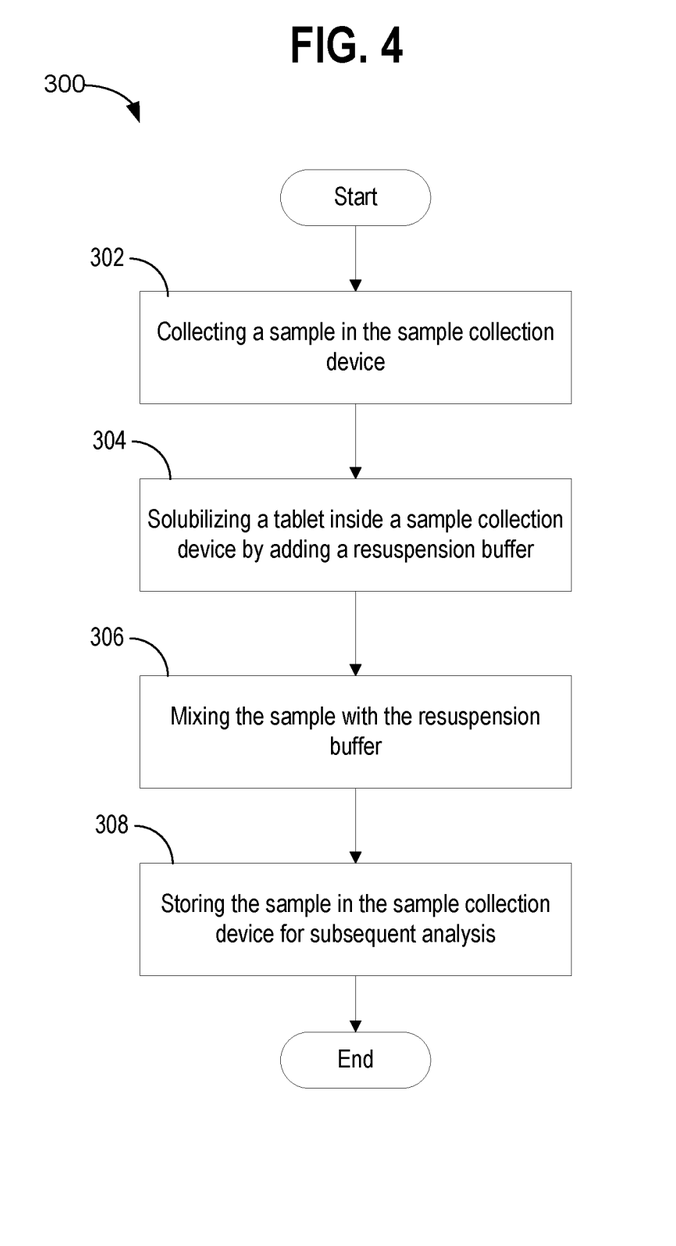
FIG. 4 illustrates a method for homogenizing a sample collected in a sample collection device.

A method 300 of homogenizing a sample in a sample collection device is illustrated in FIG. 4. In one example, the method 300 may be used with the sample collection device illustrated in FIG. 1, wherein a reagent may be placed inside the sample collection device. The reagent may be present in the container 12, inside the reagent housing 112 or inside the main chamber of the container 12. The reagent may be a tablet containing a mucolytic agent for reducing viscosity of the sample collected inside the sample collection device. The tablet may be of the composition listed in Table 1 including, NALC, $K_2HPO_4$, L-Leucine, TSC, and polyethylene glycol.

The method 300 begins at 302 by collecting a sample inside the sample collection device containing the tablet. The sample may be a biological sample, such as a body fluid from the respiratory tract, the digestive tract etc. The sample collected may be viscous due to mucus present in the sample. In one example, the mucus may be generated due to a bacterial or viral infection. The sample may be collected by opening the cap and introducing the sample into the container of the sample collection device. After collecting the sample, the cap may be coupled back to the opening of sample collection device.

The method 300 proceeds to 304, solubilizing the tablet present inside the sample collection device. Solubilizing the tablet includes adding a resuspension buffer inside the sample collection device and closing the sample collection tube by coupling to the cap, such that the tablet is at least partly submerged in the resuspension buffer. In one example, 3 ml resuspension buffer may be added inside the sample collection device containing the tablet inside the reagent housing. The resuspension buffer may be of the formulation listed in Table 2.

In one example, the resuspension buffer may be added to the reagent housing 112 containing the tablet. The tablet submerged at least partly in the resuspension buffer may be mixed by inverting the sample collection device with the cap attached. In other examples, the sample collection device may be agitated, vortexed, or placed on a shaker. The tablet may dissolve completely in the resuspension buffer. The dissolution time may be between 1.0-1.3 minutes. Dissolution of the tablet in the resuspension buffer results in releasing the constituents of the tablet including NALC in the solution. The resuspension buffer pH after dissolving the tablet may be between pH 6.2-6.4 (illustrated in FIG. 3), which is close to the physiological pH of 7-7.5.

The method 300 proceeds to 306, mixing the collected sample with the dissolved tablet in the resuspension buffer. In one example, dissolving the tablet in the resuspension buffer in the reagent housing of the sample collection device 10 may result in flowing of the resuspension buffer with the dissolved tablets through one or more apertures in the cage 126, as discussed above with reference to FIG. 1. The sample collected inside the sample collection device may be exposed to the constituents of the tablet in the resuspension buffer. In other examples, the sample and the constituents of the tablet in the resuspension buffer may be caused to come into physical contact by manipulating the container. For example, the capped container of the sample collection device may be inverted to cause the sample to mix with the resuspension buffer. In other examples, the capped container may be shaken or agitated such that the sample comes into repeated and/or active contact with the resuspension buffer.

Upon mixing of the sample with the resuspension buffer, the mucolytic agent in the tablets (NALC) may be at a concentration where it may cause mucolysis, decreasing the viscosity of the sample along with increasing the homogeneity of the sample due to easier flow and mixing.

The method 300 proceeds to 308, storing the sample mixed with the resuspension buffer and the dissolved tablet until further analysis of the sample is carried out, for example, analyzing by molecular techniques like PCR, antibody based test etc. for diagnosing a specific disease condition. The constituents if the tablet and the resuspension buffer may be configured not to interfere with subsequent diagnostic tests, specifically those utilizing polymerase chain reaction and transcription-mediated amplification technologies. In one example, storing the sample may include placing the sample collection device with the sample and the reconstituted tablet in the receiving base 14 of FIG. 1 and storing the sample collection device either at room temperature, or at 4° C., or freezing the sample. The method 300 then ends.

The above-described mucolytic tablet may be included in a kit, for example, in a kit for diagnosing microbial infection. The mucolytic tablet may have a composition described above and may be present in the kit inside a reagent chamber of a sample collection device (for example, the sample collection device 10 with the reagent housing 112). The sample collection device 10 with the tablet may be packaged in the kit, and a resuspension buffer may be included in a separate tube or vial in the kit. Additionally, other buffers and reagents may be present inside the kit along with an instruction sheet providing direction for using the kit.

In another example, a kit may include a mucolytic tablet in a sealed package. The mucolytic tablet may be introduced into a sample collection device after removing from the sealed package. In a further example, the tablets may be present inside a sample collection device, for example, inside a reagent chamber of the sample collection device. The resuspension buffer and other buffers and reagents provided in the kit may be introduced into the sample collection device as per instructions provided in the instruction sheet in the kit. In one example, the kit may be a kit for processing samples for diagnosis of tuberculosis. The kit may include the mucolytic tablet of above-described composition for reducing viscosity of respiratory tract mucus samples for diagnosis of tuberculosis.

An example kit for processing samples for diagnosis of microbial infection, such as Mycobacteria infection, may include one or more digestion and decontamination reagents. In one example, the digestion and decontamination reagents may be four different concentrations of 2%, 2.5%, 3% and 4% sodium hydroxide solution (NaOH), each solution with 1-2% of TSC, and a pH indicator (for example, phenol red). In another example, 2-4% sodium hydroxide solution, and 0-4% of a chelating agent (sodium citrate or similar) may be included in the kit. The kit may also include a neutralizing buffering reagent, which may include a source of phosphates (for example, 67 mM phosphates) and 0-0.6% citric acid. The kit may include a resuspension buffer, similar to the resuspension buffer listed in Table 2. In addition, mucolytic tablets, sample collection device and chemicals like dithiothreitol (DTT), and TSC may be packaged in the kit.

In one example, a mucolytic tablet for a sample collection device may include 15% to 65% by weight of N-acetyl L-cysteine (NALC), 6% to 30% by weight of a buffering agent, 10% to 14% by weight of a water soluble anti-adherent, and 2% to 10% by weight of at least one chelating and lubricating agent, wherein the mucolytic tablet solubilizes in a resuspension buffer. In one example, mucolytic tablet includes 55% to 65% by weight of NALC. The buffering agent in an example may be dipotassium hydrogen phosphate. In another example, the water-soluble anti-adherent in the mucolytic tablet may be L-Leucine. In a further example, the at least one chelating and lubricating agent in the mucolytic tablet may be polyethylene glycol. In yet another example, the at least one chelating agent in the mucolytic tablet may be sodium citrate. The mucolytic tablet may be prepared by applying a compression force between 3.5-4.5 pascal. The resuspension buffer may include between 60 mM to 67 mM phosphates, and 56-60 mM sodium citrate, wherein the phosphates of the resuspension buffer are from 30-36 mM disodium hydrogen phosphate and 30-36 mM dipotassium hydrogen phosphate. A weight of the mucolytic tablet may range between 0.045-0.055 grams. In an example, a time for dissolving the mucolytic tablet in 3-6 ml of the resuspension buffer ranges between 1.00-1.3 minutes. A concentration of NALC in 3 ml of resuspension buffer with the dissolved mucolytic tablet may be 4 to 6 mg/ml.

An example method of preparing a mucolytic tablet may include premixing constituents of a mucolytic tablet, followed by desiccating the premixed constituents. The premixed constituents may include 15% to 65% by weight of N-acetyl L-cysteine (NALC), 6% to 30% by weight of a buffering agent, 10% to 14% by weight of a water-soluble anti-adherent, 2% to 10% by weight of at least one chelating and lubricating agent. The method may include preparing the mucolytic tablets from the desiccated premixed constituents. In one example, desiccating the premixed constituents includes desiccating under vacuum between 26° C.-28° C. for 20 hours-2 weeks. In an example, preparing the mucolytic tablet includes using a tablet-punching machine at a speed between 25.5-40.5 g/second with a compression force between 3.5-4.5 pascal.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

EXAMPLES

The invention may be better understood by reference to the examples described below, which serve to illustrate but not to limit the present invention.

Example 1

Mucolytic NALC tablets of the formulation described above in Table 1 were each suspended in a resuspension buffer (the formulation listed in Table 2). Each of the NALC tablet was present inside a sample collection device (for example, similar to the sample collection device illustrated in FIG. 1). 6 ml resuspension buffer was introduced into each sample collection device containing one tablet. In addition, 1 ml phosphate buffer solution (PBS), representing a biological sample, was added to the NALC tablet and the resuspension buffer in each sample collection device. The above solutions were mixed by manually shaking, and inverting the sample collection device. Dissolution time of each tablet was noted and pH of the solution after dissolution of the tablet was measured and is listed in Table 3 below.

TABLE 3

Dissolving time of the tablets and pH

| Tablet | Weight (g) | Dissolving time (min) | pH |
|---|---|---|---|
| 1 | 0.048 | 1.25 | 6.35 |
| 2 | 0.046 | 1.15 | 6.36 |
| 3 | 0.047 | 1.2 | 6.27 |
| 4 | 0.046 | 1.25 | 6.28 |
| 5 | 0.042 | 1.05 | 6.39 |
| 6 | 0.047 | 1.15 | 6.34 |

The results shown in Table 3 are also illustrated in the graph 200 in FIG. 3. The columns 204 show the dissolution time (in minutes) along the first Y-axis Y1 of each of the tablets (with tablet ID 1-6). The tablets 1-6 each weigh between 0.042 g-0.048 g with an average weight of 0.046 g±0.002 g. The line 202 shows the pH along the second Y-axis Y2 of each tablet after dissolution in the resuspension buffer. The average dissolution time of the NALC tablet in the resuspension buffer and the saline is 1.2 min±0.07 min and the pH is 6.3±0.04. The results indicate that the NALC tablet have a fast dissolution time and provides a pH close to the physiological pH 7, which may not adversely alter/degrade/damage the constituents of the biological sample.

Example 2

Storage and long term stability of the mucolytic tablet was tested. Composition of the mucolytic tablet being tested included 60% by weight of NALC, 23% by weight of a buffering agent $K_2HPO_4$, 12% by weight of a water-soluble anti-adherent L-Leucine, and 6% by weight of a chelating and lubricating agent polyethylene glycol. The shelf life of the tablet was assessed by doing a colorimetric assay using a spectrophotometer.

Each of the tablets being tested for stability and shelf life was stored in individual vials or tubes with a sealed cap for specific time. At beginning of storage, each tablet was weighed and the corresponding NALC amount by weight in the tablet was calculated based on the composition of the tablet. At end of a specified storage time, NALC amount in each of the tablets was calculated by suspending each tablet in 6 ml of resuspension buffer, followed by measuring absorbance of the resuspension buffer. Absorbance was measured at a wavelength of 593 nM. Additionally, a NALC standard curve was generated using different concentrations of NALC (0 μM to 60 μM) dissolved in the resuspension buffer (resuspension buffer formulation listed in Table 2) and absorbance was measured at 593 nM wavelength. The absorbance of the tablet being tested was then compared to the standard curve of NALC to determine the amount of NALC in each tablet at the end of the storage period. The results in Table 4 show NALC amount in tablets stored in sealed vials for up to 30 months at ambient temperature.

TABLE 4

NALC amount in stored mucolytic tablets.

| Average Tablet wieght (grams) | Storage Time (months) | Calculated NALC at beginning of storage (mg) | Absorbance based NALC at end of storage (mg) |
|---|---|---|---|
| 0.048 ± 0.002 | 10 months | 29.22 ± 1.7 | 30.8 ± 1.9 |
| 0.048 ± 0.0018 | 15 months | 29.2 ± 1.1 | 29.01 ± 2.1 |
| 0.05 ± 0.001 | 20 months | 30.46 ± 0.81 | 33.9 ± 1.3 |
| 0.048 ± 0.003 | 25 months | 29.32 ± 1.89 | 28.8 ± 2.1 |
| 0.046 ± 0.0006 | 28 months | 27.6 ± 0.36 | 32.08 ± 2.6 |
| 0.05 ± 0.001 | 30 months | 30.12 ± 0.6 | 31.2 ± 1.4 |

Results in Table 4 show that the NALC amount at end of the storage period of 30 months is in the range of 25 mg-35 mg per tablet, which is similar to the NALC amount in the beginning of the storage period (25 mg-35 mg/tablet). These results show that the mucolytic tablets have a shelf life of at least 30 months, wherein the mucolytic tablets may be stored in a sealed vial at ambient temperature without compromising NALC amount in the tablet.

Example 3

The biological sample collected in the sample collection device may be used for assays like PCR, for example, to detect a certain microbial nucleic acids (bacterial or viral DNA and/or RNA), for diagnosing diseases. Hence, the constituents of the mucolytic tablets released in the resuspension buffer may be configured to not interfere with the PCR reaction. The effect of the mucolytic tablets on a polymerase chain reaction (PCR) amplifying a segment of DNA was tested, as described below.

A plasmid (ATS380 Mtb) was used as a template for the PCR reaction. Plasmid DNA was prepared using standard DNA preparation protocol. Dilutions of the plasmid DNA (($10^9-10^4$) plasmids) were made and 1 µl of diluted plasmid DNA was used in each tube for 50 µl PCR reaction. The PCR reactions in each tube included a known concentration of plasmid DNA template, a forward primer (10 µM) and a reverse primer (10 µM) targeted to the plasmid DNA, DNA polymerase, dNTPs 2.5 mM, 5×PCR reaction buffer, in absence or presence of a mucolytic tablet dissolved in a resuspension buffer (or in absence or presence of the resuspension buffer 5 mg/ml). Molecular grade water was added to bring volume of each PCR reaction to 50 µl.

The PCR reactions conditions included, denaturing at 98° C. for 50 seconds, followed by 25 cycles of [98° C. 10 sec, 66° C. 30 sec, and 72° C. for 30 sec], and followed by 72° C. for 3 minutes. The PCR reaction was carried out in a thermocycler. Each PCR reaction was run on a 1.2% agarose gel containing EtBr and the agarose gel was observed under a source of UV light for an amplified PCR product (of approximately 650 base pairs).

The results showed that the PCR product formed in presence of the mucolytic tablet was of similar intensity/same intensity as a corresponding PCR product without the mucolytic tablet for the same dilution of the DNA template. Similarly, the PCR product amplification was not altered in the presence of the resuspension buffer in the PCR reaction. These results indicate that constituents of the tablet and the resuspension buffer do not interfere in the molecular detection of even every low amounts of DNA by PCR.

The invention claimed is:

1. A mucolytic tablet for a sample collection device, comprising:
   (i) 15% to 65% by weight of N-acetyl L-cysteine (NALC);
   (ii) 6% to 30% by weight of a buffering agent;
   (iii) 10% to 14% by weight of a water soluble anti-adherent; and
   (iv) 2% to 10% by weight of at least one water soluble chelating and lubricating agent,
   wherein the mucolytic tablet solubilizes in a resuspension buffer.

2. The mucolytic tablet of claim 1, wherein the mucolytic tablet includes 55% to 65% by weight of NALC.

3. The mucolytic tablet of claim 1, wherein the buffering agent is dipotassium hydrogen phosphate.

4. The mucolytic tablet of claim 1, wherein the water soluble anti-adherent is L-Leucine.

5. The mucolytic tablet of claim 1, wherein the at least one water soluble chelating and lubricating agent is polyethylene glycol.

6. The mucolytic tablet of claim 1, wherein the at least one water soluble chelating and lubricating agent is sodium citrate.

7. The mucolytic tablet of claim 1, wherein the mucolytic tablet is prepared by applying a compression force between 3.5-4.5 pascal.

8. The mucolytic tablet of claim 1, wherein the resuspension buffer includes 60 mM to 67 mM phosphates, and 56-60 mM sodium citrate.

9. The mucolytic tablet of claim 8, wherein the phosphates of the resuspension buffer are from 30-36 mM disodium hydrogen phosphate and 30-36 mM dipotassium hydrogen phosphate.

10. The mucolytic tablet of claim 1, wherein a weight of the mucolytic tablet is between 0.045-0.055 grams.

11. The mucolytic tablet of claim 10, wherein the mucolytic tablet dissolves in 3-6 ml of the resuspension buffer in between 1.00-1.3 minutes, and wherein the resuspension buffer comprises at least one source of phosphates and one or more chelating agents.

12. The mucolytic tablet of claim 11, wherein, upon dissolution of the mucolytic tablet, a concentration of NALC released from the mucolytic tablet into the resuspension buffer is 4 to 6 mg/ml.

13. The mucolytic tablet of claim 11, wherein the buffering agent maintains a pH of between 6.2-6.5 in solution when the mucolytic tablet is dissolved in the resuspension buffer.

14. A method, comprising:
   premixing constituents of a mucolytic tablet, followed by desiccating the premixed constituents, the premixed constituents including:
   (i) 15% to 65% by weight of N-acetyl L-cysteine (NALC);
   (ii) 6% to 30% by weight of a buffering agent;
   (iii) 10% to 14% by weight of a water soluble anti-adherent;
   (iv) 2% to 10% by weight of at least one chelating and lubricating agent; and
   preparing the mucolytic tablet from the desiccated premixed constituents.

15. The method of claim 14, wherein desiccating the premixed constituents includes desiccating under vacuum between 26° C.-28° C. for 20 hours-2 weeks.

16. The method of claim 14, wherein preparing the mucolytic tablet includes using a tablet-punching machine at a speed between 25.5-40.5 g/second with a compression force between 3.5-4.5 pascal.

17. The method of claim 14, wherein the mucolytic tablet weighs between 0.045-0.055 grams.

18. The method of claim 14, wherein the premixed constituents include 55% to 65% by weight of NALC, 6% to 30% by weight of $K_2HPO_4$, 4% to 15% by weight of L-Leucine, and 2% to 10% by weight of polyethylene glycol.

19. A sample collection device, comprising:
a container with a closure assembly;
a reagent chamber inside the container, the reagent chamber fluidically connected to an inner volume of the container; and
a mucolytic tablet in the reagent chamber, a composition of the mucolytic tablet including:
 (i) 15% to 65% by weight of N-acetyl L-cysteine (NALC),
 (ii) 6% to 30% by weight of $K_2HPO_4$,
 (iii) 10% to 14% by weight of L-Leucine,
 (iv) 2% to 10% by weight of polyethylene glycol, and
 (v) 0% to 60% by weight of trisodium citrate.

20. The sample collection device of claim 19, wherein the reagent chamber comprises at least one perforation and wherein the at least one perforation in the reagent chamber fluidically connects the reagent chamber to the inner volume of the container.

21. A mucolytic tablet for a sample collection device, comprising:
 (i) 15% to 65% by weight of N-acetyl L-cysteine (NALC);
 (ii) 6% to 30% by weight of a buffering agent;
 (iii) 10% to 14% by weight of a water soluble anti-adherent; and
 (iv) 2% to 10% by weight of at least one chelating and lubricating agent,
wherein a weight of the mucolytic tablet is between 0.045-0.055 grams, and
wherein the mucolytic tablet solubilizes in a resuspension buffer.

* * * * *